(12) United States Patent
Marnay et al.

(10) Patent No.: US 6,206,879 B1
(45) Date of Patent: Mar. 27, 2001

(54) OSTEOSYNTHETIC HOLDING SYSTEM

(75) Inventors: Thierry Marnay, Castilnaux le lez (FR); Michael Mayer, Munich; Jens Beger, Tuttlingen, both of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/425,502

(22) Filed: Oct. 22, 1999

(30) Foreign Application Priority Data

Oct. 22, 1998 (DE) .............................................. 198 48 715

(51) Int. Cl.[7] .................................................. A61B 17/56
(52) U.S. Cl. .................................................................. 606/53
(58) Field of Search ................................ 606/53, 54, 59, 606/61, 62, 70, 71

(56) References Cited

U.S. PATENT DOCUMENTS

| | | | | |
|---|---|---|---|---|
| 3,997,138 | * | 12/1976 | Crock et al. | 248/67.5 |
| 4,258,708 | * | 3/1981 | Gentile | 128/92 A |
| 4,620,533 | * | 11/1986 | Mears | 128/92 Z |
| 4,648,388 | * | 3/1987 | Steffee | 128/69 |
| 4,653,481 | | 3/1987 | Howland et al. | |
| 5,030,220 | * | 7/1991 | Howland | 606/61 |
| 5,112,332 | * | 5/1992 | Cozard et al. | 606/61 |
| 5,330,473 | * | 7/1994 | Howland | 606/61 |
| 5,582,612 | * | 12/1996 | Lin | 606/61 |
| 5,591,166 | * | 1/1997 | Bernhardt et al. | 606/61 |
| 5,613,968 | * | 3/1997 | Lin | 606/61 |

FOREIGN PATENT DOCUMENTS 36 24 067 2/1987 (DE) .
195 10 543 10/1996 (DE) .

* cited by examiner

*Primary Examiner*—Gene Mancene
*Assistant Examiner*—Eduardo C. Robert
(74) *Attorney, Agent, or Firm*—Barry R. Lipsitz

(57) ABSTRACT

An osteosynthetic holding system is provided which comprises bone anchoring elements, each of which has a clamping element as well as two receptacles arranged thereon for receiving holding bars. The receptacles have blocking elements arranged thereon which define accesses to the receptacles. Two holding bars are provided which are insertable into the receptacles of each bone anchoring element. The clamping element can be tightened to clamp the two holding bars against the receptacles, thereby fixing the position of each bone anchoring element with respect to the other. The blocking elements, together with the clamping element in a tightened state, constrict the accesses to said receptacles in a direction transverse to a longitudinal direction of the holding bars such that the holding bars no longer fit through the accesses. The blocking elements of the two receptacles are dimensioned such that upon releasing the clamping element, the accesses to the two receptacles are enlarged to enable each of the holding bars to fit through its respective receptacle in turn as the clamping element is released.

10 Claims, 4 Drawing Sheets

OSTEOSYNTHETIC HOLDING SYSTEM

BACKGROUND OF THE INVENTION

The present disclosure relates to the subject matter disclosed in German patent application No. 198 48 715.0 of Oct. 22, 1998, the entire specification of which is incorporated herein by reference.

The invention relates to an osteosynthetic holding system with bone anchoring elements comprising two receptacles arranged alongside each other for one holding bar each and a clamping element, which in the tightened state thereof clamps the two holding bars against the receptacles, and with blocking elements which together with the clamping element in the tightened state thereof constrict the access to the receptacles in a direction transverse to the longitudinal direction of the holding bars such that the holding bars no longer fit through the access.

Such osteosynthetic holding systems are used for fixing the position of bone parts relative to one another. Bone anchoring elements, for example, in the form of bone screws, hooks, etc., are inserted into the bone parts to be fixed, and these bone anchoring elements are fixed relative to one another via holding bars.

In osteosynthetic holding systems, it is known to join the bone anchoring elements together by two parallel bars which are inserted into receptacles on the bone anchoring elements and are clamped against these receptacles by clamping elements on the bone anchoring elements. With the clamping element in the released state, it is thus possible, to bring the bone anchoring elements into the desired position relative to each other and using two bars to then fix this position in a very stable and lasting manner by tightening the clamping element.

In order to already fix the holding bars at least loosely in their position in the receptacles before tightening the clamping elements, it is, furthermore, known to provide the receptacles with blocking elements which make the access to the receptacles, which is determined by these blocking elements, on the one hand, and by the clamping element, on the other hand, so narrow that the holding bars are held undetachably in the receptacle when the clamping element is not completely released but is already close to the end position in which the clamping occurs. Therefore, only when the clamping element is completely released can the holding bars be removed from or inserted into the receptacle.

This narrowing of the access also serves to ensure that the holding bars remain securely in the clamped position in the receptacle.

Thus, in the known holding systems of this kind both holding bars are inserted before tightening the clamping elements. The clamping elements are then tightened up to a position in which the holding bars are held undetachably, but are not yet clamped against the receptacle. If, in this situation, work has still to be done on the bone fragments or the bone anchoring elements have to be adjusted, this may obstruct the operator to a certain extent as both holding bars are inserted in the receptacles and may, under certain circumstances, cover the operating area.

The object of the invention is to design an osteosynthetic holding system of the generic kind so as to prevent an obstruction by the two undetachably inserted holding bars prior to the final tightening of the holding system.

SUMMARY OF THE INVENTION

This object is accomplished in accordance with the invention in an osteosynthetic holding system of the kind described at the outset in that the blocking elements of the two receptacles are of such different dimensions that upon releasing the clamping element the accesses to the two receptacles are so enlarged one after the other that the holding bars fit through these.

In other words, the accesses to the two receptacles differ in size. Consequently, with the clamping element tightened, both accesses are so narrow that holding bars no longer fit through them, in an intermediate position the access of only one receptacle is large enough for the holding bar to fit through it, and only with the clamping element completely released are the accesses to both receptacles large enough for the holding bars to fit through them. It is thereby made possible to first join bone anchoring elements to one another using one holding bar only and to fix it undetachably but loosely on the bone anchoring elements and to insert the second holding bar only at a later point in time and then clamp it together with the previously inserted holding bar to the bone anchoring elements.

The clamping element for clamping the two holding bars against their receptacles may vary as regards its construction. For example, eccentric clamping elements could be screwed onto the bone anchoring elements. It is particularly advantageous for the clamping element to be a clamping nut which is screwed onto an external thread of the bone anchoring element.

Provision is made in a preferred embodiment for the receptacles to be of groove-shaped construction and for the edge regions of the groove-shaped receptacles to form the blocking elements. These edge regions in the two receptacles of a bone anchoring element thus have different dimensions and form together with the clamping element accesses of varying width to the receptacles.

In particular, provision may be made for the free edges of the two groove-shaped receptacles to differ in height.

The following description of preferred embodiments of the invention serves in conjunction with the appended drawings to explain the invention in greater detail.

Figure 1:
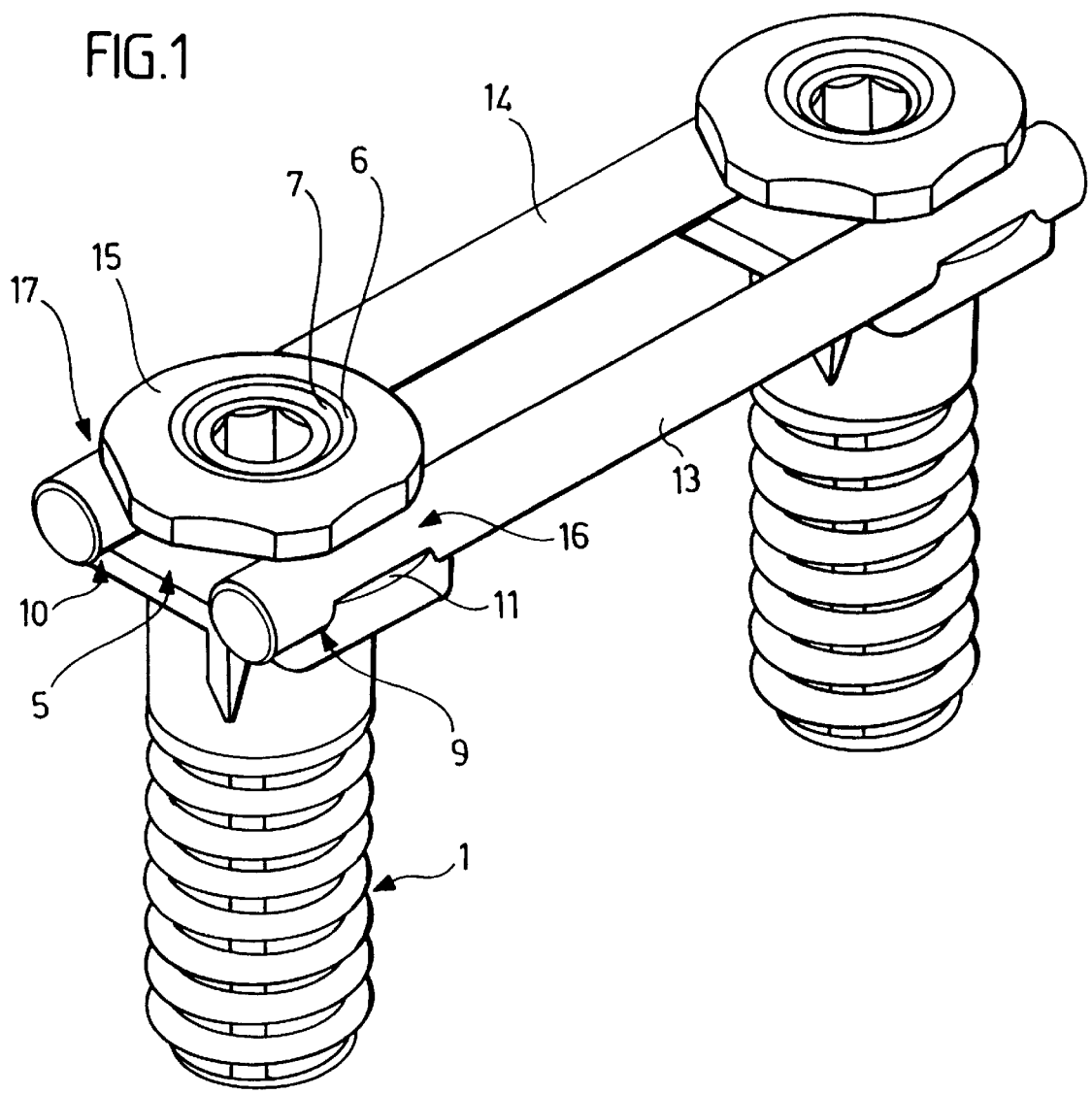
FIG. 1 an osteosynthetic holding system with two bone anchoring elements and two holding bars.
Figure 2:
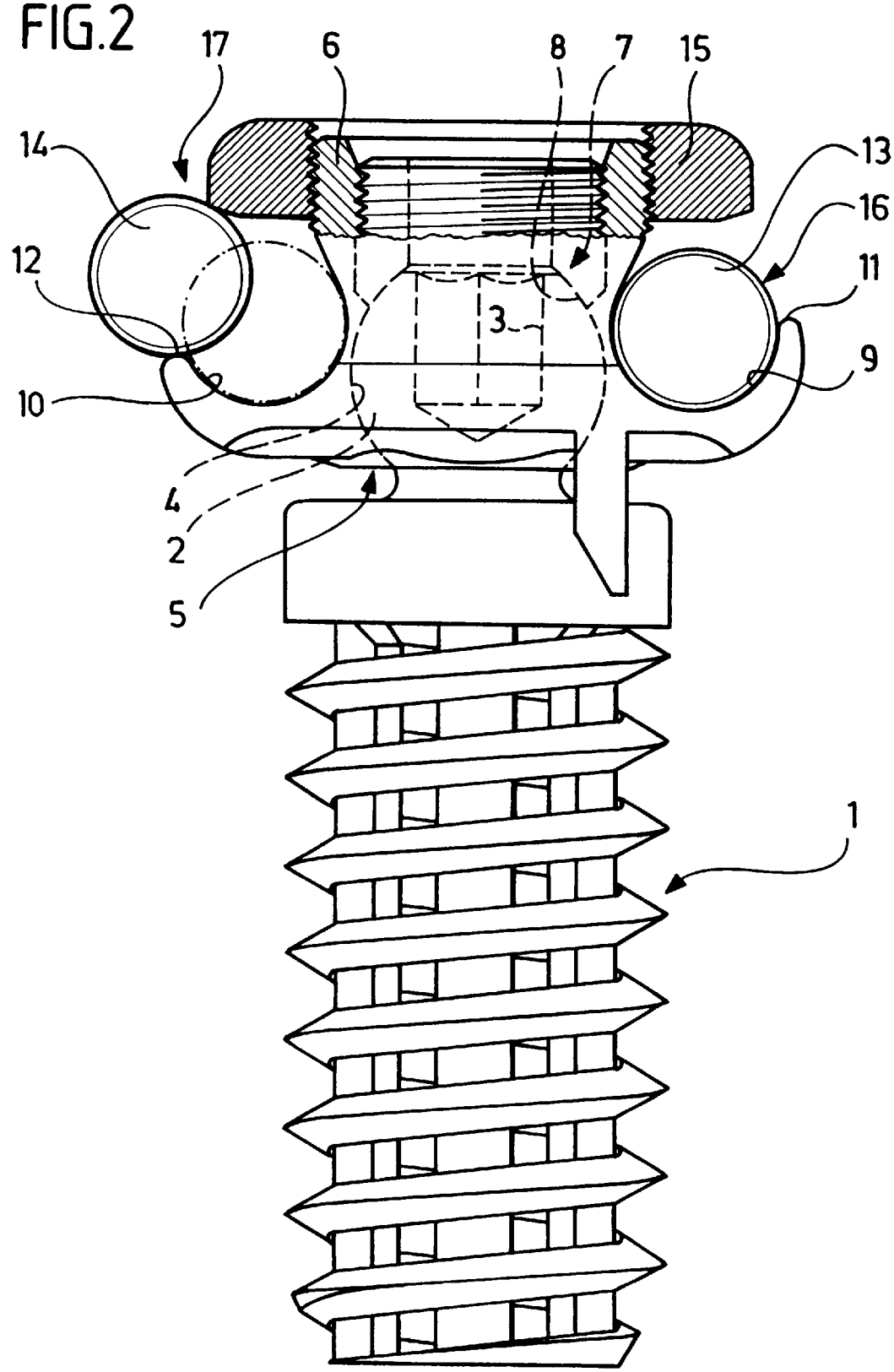
FIG. 2 a longitudinal sectional view of a bone anchoring element with a partly released clamping element and two inserted holding bars.

The osteosynthetic holding system shown in FIGS. 1 and 2 comprises two hollow bone screws 1 with a spherical head 2 which has a non-circular insert opening 3 for a screwing-in tool which is not shown in the drawings.

The spherical head 2 extends through a central opening 4 of a receiving plate 5 which surrounds and engages under the spherical head 2 and carries an upwardly projecting threaded connection piece 6 adjoining the central opening 4. Screwed into this threaded connection piece 6 is a clamping ring 7 which is supported with its free edge on the spherical head 2 of the hollow bone screw 1 and which in the tightly screwed-in state thus clamps the spherical head 2 between the receiving plate 5, on the one hand, and itself, on the other hand. When the clamping ring 7 is released the receiving plate 5 is thus pivotable relative to the hollow bone screw 1 and is fixable in any desired angular position by screwing in the clamping ring 7.

The receiving plate 5 comprises on opposite sides thereof groove-shaped or channel-shaped receptacles 9, 10 of circular-arc-shaped cross section, which extend parallel to each other and are arranged at the same height. The two receptacles 9 and 10 are open in the upward direction. Their dimensions are identical, but the height of the free edge 11, 12 is different. In one receptacle 9, the free edge 11 is of higher construction than in the other receptacle 10.

Holding bars 13, 14 of circular cross section with identical dimensions can be inserted from the side into these receptacles 9 and 10.

Screwed onto an external thread of the threaded connection piece 6 is a clamping nut 15. When the clamping nut 15 is firmly tightened, the underside thereof comes to rest against the upper side of the two holding bars 13 and 14 and thereby presses these into and clamps them firmly in the receptacles 9 and 10.

There is formed between the free edges 11 and 12 of the receptacles 9 and 10, respectively, on the one hand, and the underside of the clamping nut 15, on the other hand, for both receptacles, an access 16 and 17, respectively, which in the firmly screwed-on state of the clamping nut 15 is so narrow that the holding bars 13 and 14 do not fit through it. Therefore, the holding bars 13 and 14 cannot be removed from the receptacles 9 and 10.

When the clamping nut 15 is screwed out of the clamping position, the accesses 16 and 17 thus become wider, and owing to the different height of the free edges 11 and 12, the width of the accesses is different. As the free edge 12 is of lower construction than the free edge 11, the access 17 will first attain a width which enables the holding bar 14 to be removed from the receptacle 10 or inserted into the receptacle 10 through the access 17, whereas the other holding bar 13 does not yet fit through the access 16.

Only when the clamping nut 15 is screwed off further does the access 16 become wide enough for the holding bar 13 to fit through it.

In order to construct an osteosynthetic holding system, normally two bone anchoring elements, each comprising a hollow bone screw 1 with a spherical head 2, a receiving plate 5 and a clamping nut 15, are joined together by two holding bars 13 and 14.

The two hollow bone screws 1 are first screwed into the bone fragments which are to be fixed relative to one another. Initially, the clamping rings 7 are not yet tightened so the receiving plates 5 remain pivotable relative to the screwedin hollow bone screws 1. A first holding bar 13 is placed in the receptacles 9 of the two bone anchoring elements and held loosely but undetachably by screwing on the clamping nut 15. This results in a provisional, loose connection of the two bone anchoring elements, in particular, an orientation is thereby already imparted to the two receiving plates 5 relative to each other.

In this position, the operator can carry out any necessary operating steps, for example, it is possible by tightening the clamping nut 15 to clamp the one inserted holding bar 13 to both bone anchoring elements and thereby form a rigid holding system, but which only comprises one holding bar 13 and thus still leaves accesses free in the front region, for example, for insertion of a bone dowel between two bone fragments. It is also possible, with only one holding bar 13 inserted and the clamping nut 15 released to a slight extent, to change the spacing of the two bone anchoring elements relative to each other using a suitable device, for example, with the aid of a traction instrument, and to fix this spacing via the one holding bar 13 by tightening the clamping nut 15. In this position, the operator can fix the spacing of the bone fragments by other means, for example, by using bone dowels, inserting bone plates, etc.

After completion of the necessary operating steps, the clamping nut 15 is screwed off to such an extent that the access 17 to the other receptacle 10 has the necessary width for insertion of the second holding bar 14 so the latter is now inserted and together with the holding bar 13 is clamped in the associated receptacle by screwing on the clamping nut 15. During all these steps, it is ensured that the holding bar 13 which was first inserted is held undetachably in its receptacles 9. This facilitates the handling of the holding system and, in particular, also prevents the first inserted holding bar 13 from being able to be removed unintentionally from its receptacle 9.

Once the two holding bars 13 and 14 are clamped to the corresponding receptacles by the clamping nut 15, the receiving plates 5 are, in turn, rigidly connected to the associated hollow bone screws 1 by tightening the,clamping rings 7. This results in a holding system with a high degree of stability which securely fixes in their relative position the two bone fragments to be fixed relative to each other until completion of the healing process.

Figure 3:
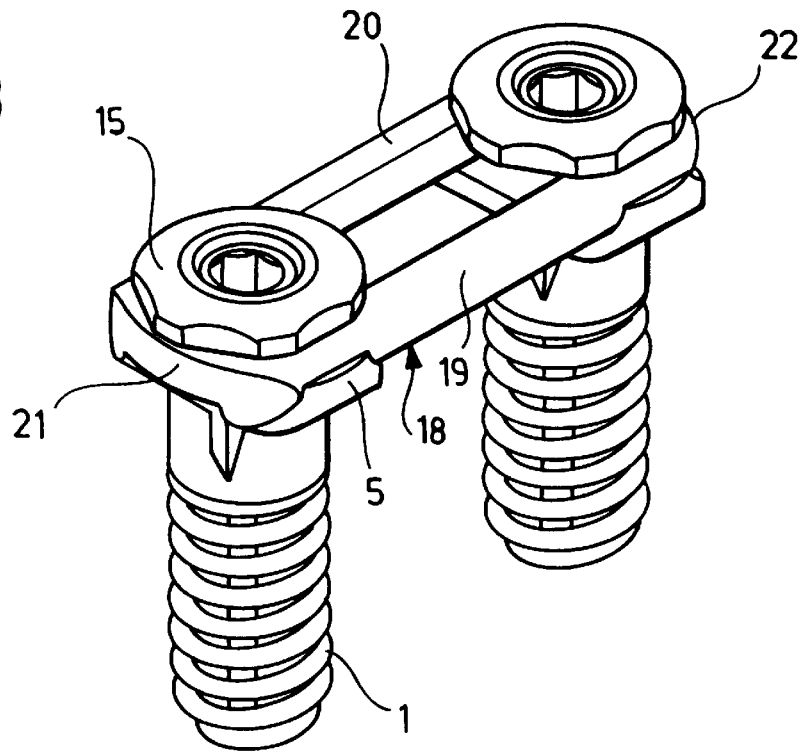
FIG. 3 a view of an osteosynthetic holding system similar to FIG. 1, wherein the holding bars are replaced by a one-part connecting plate.
Figure 4:
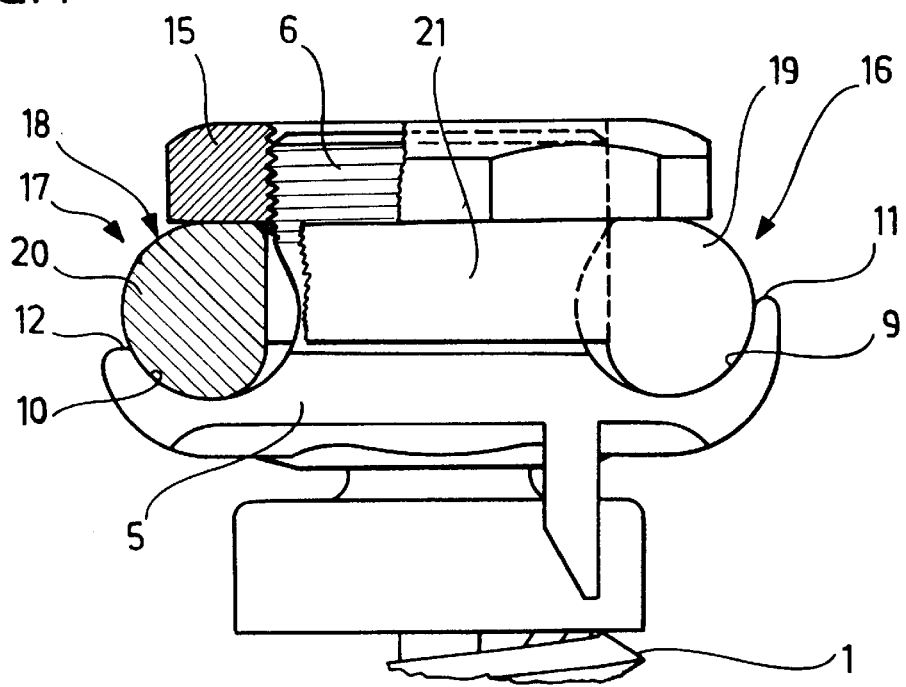
FIG. 4 a sectional view of the upper part of a bone anchoring element in the embodiment of FIG. 3.

In addition to the described use with two holding bars 13 and 14, the described holding system is also suitable for replacing these holding bars 13 and 14 by a one-part plate 18, which essentially comprises two parallel limbs 19, 20, which are permanently joined to each other via two transverse limbs 21 and 22 (FIGS. 3 and 4). With the clamping nut 15 removed, this plate 18 can be placed on the receiving plates 5 such that the two limbs 19 and 20 dip into the receptacles 9 and 10, respectively, of the receiving plates 5, and the plate 18 can then be fixed in this position by tightening the clamping nut 15.

Accordingly, the same bone anchoring elements can be used to selectively work in the described manner with two holding bars 13 and 14 or with a plate 18.

Figure 5:
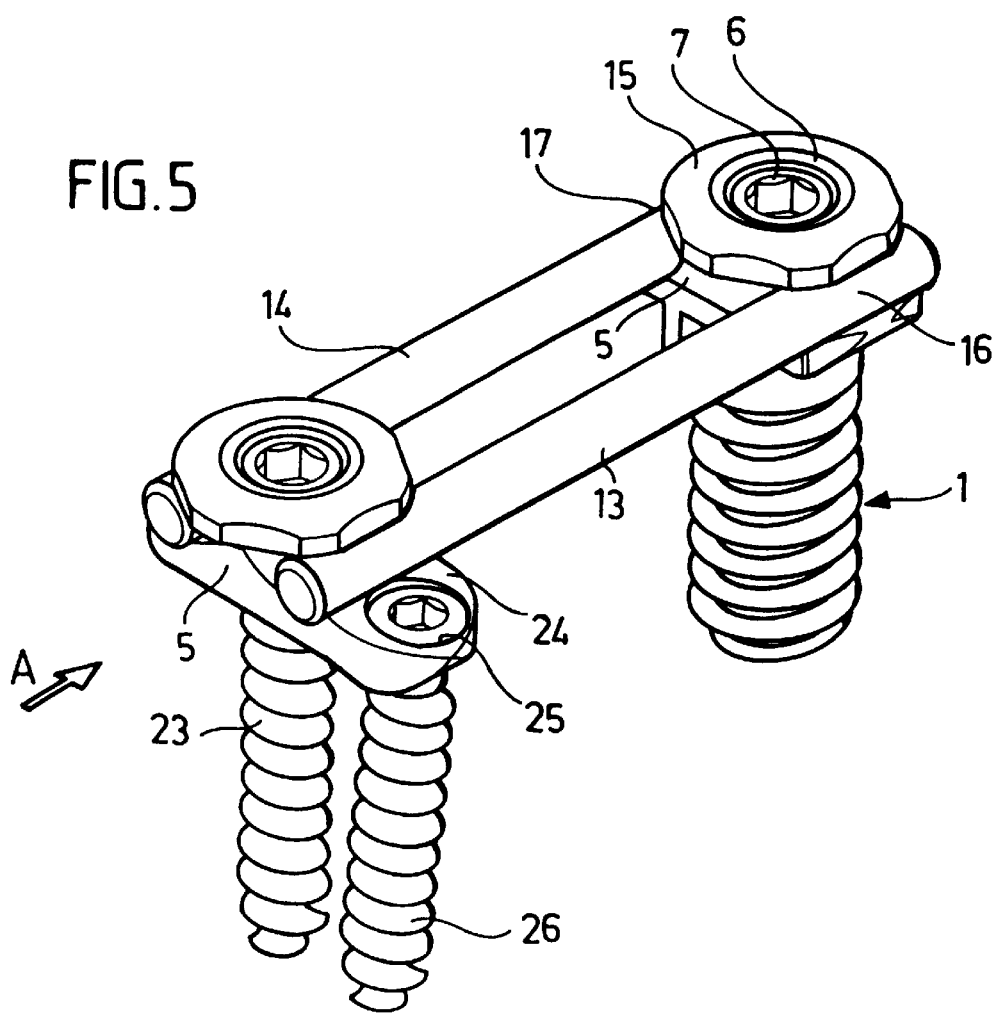
FIG. 5 an osteosynthetic holding system similar to FIG. 1 with modified bone anchoring elements.
Figure 6:
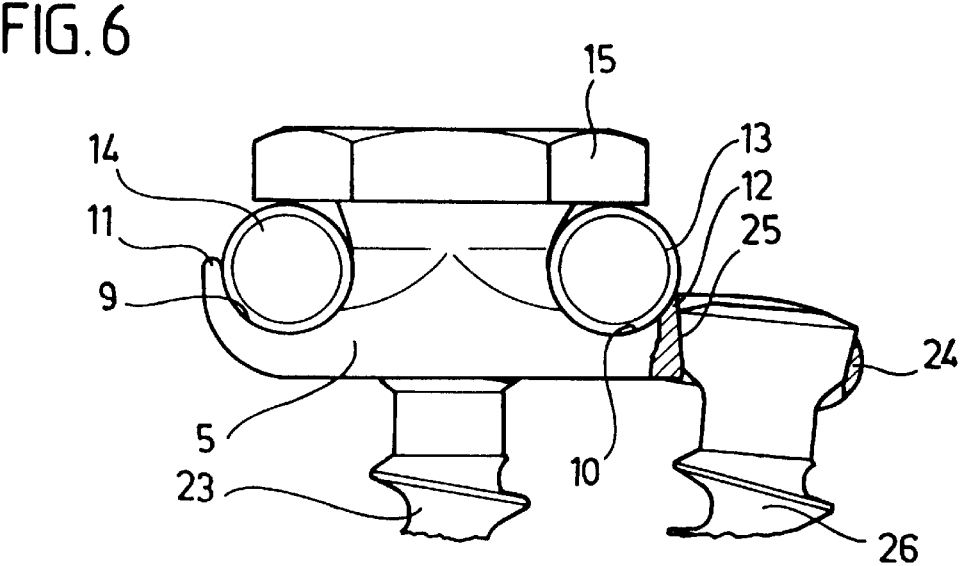
FIG. 6 a partial view of the holding system of FIG. 5 in the direction of arrow A.

FIGS. 5 and 6 show a modified embodiment of a holding system which is similar in construction to the holding system of FIGS. 1 and 2, and, therefore, like parts bear like reference numerals.

In contrast to the embodiments of FIGS. 1 and 2, in the embodiment of FIGS. 5 and 6 one of the two hollow bone screws 1 is replaced by a conventional bone screw 23 which rests with a spherical underside of a screw head on a corresponding bearing surface of the receiving plate 5.

This receiving plate 5 has at the side thereof a projecting extension 24 with a push-through opening 25 narrowing conically in the downward direction, into which a further bone screw 26 is pushed. Therefore, in this case not only one hollow bone screw 1 is held on the receiving plate 5, but instead there are pushed through this receiving plate 5 two bone screws 23 and 26 with which the receiving plate 5 can be attached to a bone.

The remaining design of the receiving plate 5 is identical to that of the embodiment of FIGS. 1 and 2. In particular, the dimensions of the receptacles 9 and 10 with the free edges 11 and 12 are chosen in the same way so that the accesses 16 and 17 are different in size and thus release the holding bars 13 and 14 one after the other.

It is, of course, also possible to replace each of the hollow bone screws 1 in the manner described with reference to FIGS. 5 and 6 by two bone screws 23 and 26.

What is claimed is:

1. An osteosynthetic holding system comprising:
   a plurality of bone anchoring elements, each having two receptacles arranged thereon;
   said receptacles each having a respective blocking element arranged thereon defining an access to the receptacle;
   respective holding bars, each of which is insertable into respective receptacles of at least two bone anchoring elements;
   a clamping element, said clamping element clamping the holding bars against said receptacles in a tightened state thereof, and together with said blocking element in the tightened state constricting the accesses to said receptacles in a direction transverse to a longitudinal direction of said holding bars such that said holding bars no longer fit through said accesses;
   wherein the blocking elements of the two receptacles are of such different dimensions that upon releasing said clamping element, the accesses to the two receptacles are so enlarged one after the other that each of said holding bars fits through its respective receptacle in turn as the clamping element is released.

2. A holding system in accordance with claim 1 wherein said clamping element comprises a clamping nut screwed onto an external thread of said bone anchoring element.

3. A holding system in accordance with claim 2, wherein said receptacles are of groove-shaped construction, and edge regions of the groove-shaped receptacles form said blocking elements.

4. A holding system in accordance with claim 3, wherein free edges of said two groove-shaped receptacles arranged on each bone anchoring element are of different height.

5. A holding system in accordance with claim 1, wherein said receptacles are of groove-shaped construction, and edge regions of the groove-shaped receptacles form said blocking elements.

6. A holding system in accordance with claim 5, wherein free edges of the two groove-shaped receptacles arranged on each bone anchoring element are of different height.

7. A bone anchoring element comprising:
   two receptacles adapted to receive holding bars;
   blocking elements arranged on each receptacle defining an access to the receptacle;
   a clamping element, said clamping element adapted for clamping the holding bars against said receptacles in a tightened state thereof, and together with said blocking element in the tightened state constricting the accesses to said receptacles in a direction transverse to a longitudinal direction of said holding bars such that said holding bars no longer fit through said accesses;
   wherein the blocking elements of the two receptacles are of such different dimensions that upon releasing said clamping element, the accesses to the two receptacles are so enlarged one after the other that each of said holding bars fits through its respective receptacle in turn as the clamping element is released.

8. A bone anchoring element in accordance with claim 7, wherein said clamping element comprises a clamping nut screwed onto an external thread of said bone anchoring element.

9. A bone anchoring element in accordance with claim 7, wherein said receptacles are of groove-shaped construction, and edge regions of the groove-shaped receptacles form said blocking elements.

10. A bone anchoring element in accordance with claim 9, wherein free edges of the two groove-shaped receptacles are of different height.

* * * * *